(12) United States Patent
Bartlett et al.

(10) Patent No.: US 9,033,508 B2
(45) Date of Patent: May 19, 2015

(54) HANDHELD VISION TESTER AND CALIBRATION THEREOF

(75) Inventors: Michael Bartlett, Richardson, TX (US);
William R. Krenik, Garland, TX (US);
Yi-Zhong Wang, Plano, TX (US)

(73) Assignee: VITAL ART AND SCIENCE, LLC, Richardson, TX (US)

( * ) Notice: Subject to any disclaimer, the term of this patent is extended or adjusted under 35 U.S.C. 154(b) by 506 days.

(21) Appl. No.: 13/319,317

(22) PCT Filed: May 7, 2010

(86) PCT No.: PCT/US2010/034086
§ 371 (c)(1),
(2), (4) Date: Nov. 7, 2011

(87) PCT Pub. No.: WO2010/132305
PCT Pub. Date: Nov. 18, 2010

(65) Prior Publication Data
US 2012/0050686 A1 Mar. 1, 2012

Related U.S. Application Data

(60) Provisional application No. 61/176,885, filed on May 9, 2009.

(51) Int. Cl.
*A61B 3/02* (2006.01)
*A61B 3/032* (2006.01)
*A61B 3/00* (2006.01)

(52) U.S. Cl.
CPC .............. *A61B 3/032* (2013.01); *A61B 3/0066* (2013.01); *A61B 3/0033* (2013.01); *G09G 2380/08* (2013.01)

(58) Field of Classification Search
CPC .... A61B 3/0033; A61B 3/005; A61B 3/0066; A61B 3/02; A61B 3/024; A61B 3/028; A61B 3/18
USPC .......................................... 351/222–224, 246
See application file for complete search history.

(56) References Cited

U.S. PATENT DOCUMENTS 4,486,180 A 12/1984 Riley
4,750,830 A 6/1988 Lee
(Continued)

FOREIGN PATENT DOCUMENTS

JP 2002209851 A 7/2002
JP 2003290144 A 10/2003
(Continued)

OTHER PUBLICATIONS

Wiemer, Nanouk, G.M., "Refractive Properties of the Healthy Human Eye During Acute Hyperglycemia," Graef's Archive for Clinical and Experimental Opthamology, 246(7): 993-8, Apr. 2008, URL:http://www.ncbi.nim.nih.gov/pmc/articles/PMC2413123/, entire document.
(Continued)

*Primary Examiner* — Huy K Mai

(57) ABSTRACT

In one aspect, there is provided a handheld vision tester comprising a display, cursor control, interface port, and camera. The display delivers a series of images making up vision tests to a user who interacts with the vision tests by using the display and cursor control of the handheld vision tester. The camera verifies the user is taking the vision tests. The results of the vision tests are stored in the handheld communication device. The interface port allows for communication of the stored results of the vision tests with external devices. In another aspect, there is provided a calibration system for the handheld vision tester. The calibration system includes a stand to hold the handheld vision tester and a reflective surface substantially parallel to a display of the handheld vision tester.

14 Claims, 4 Drawing Sheets

(56) References Cited

U.S. PATENT DOCUMENTS

| | | |
|---|---|---|
| 6,542,081 B2 | 4/2003 | Torch |
| 6,656,131 B2 | 12/2003 | Alster et al. |
| 7,220,000 B2 | 5/2007 | Alster et al. |
| 7,275,830 B2 | 10/2007 | Alster et al. |
| 7,367,675 B2 | 5/2008 | Maddalena et al. |
| 7,448,753 B1 | 11/2008 | Chinnock |
| 7,665,847 B2 | 2/2010 | Alster et al. |
| 7,789,510 B2* | 9/2010 | Fateh .......................... 351/203 |
| 8,162,919 B2 | 4/2012 | Cull et al. |
| 8,444,270 B2 | 5/2013 | Nordstrom |
| 2003/0157464 A1 | 8/2003 | Tanassi et al. |
| 2007/0200927 A1 | 8/2007 | Krenik |
| 2009/0257189 A1* | 10/2009 | Wang et al. ............. 361/679.56 |

FOREIGN PATENT DOCUMENTS

| | | | |
|---|---|---|---|
| JP | 2004537331 | A | 12/2004 |
| JP | 2005313003 | A | 11/2005 |
| JP | 2010528705 | A | 8/2010 |
| JP | 2012510883 | A | 5/2012 |
| WO | 02076301 | A1 | 10/2002 |
| WO | 2007026368 | A2 | 3/2007 |
| WO | 2008128192 | A1 | 10/2008 |
| WO | 2008155544 | A1 | 12/2008 |
| WO | 2010132304 | A1 | 11/2010 |
| WO | 2010132305 | A1 | 11/2010 |

OTHER PUBLICATIONS

European Search Report dated Apr. 17, 2014, Application No. 10775299.0-1660, Applicant: Vital Art and Science Incorporated, 10 pages.

Foreign Communication From a Related Counterpart Application, Japanese Application No. 2012-510884, Japanese Office Action dated Dec. 24, 2013, 2 pages.

* cited by examiner

HANDHELD VISION TESTER AND CALIBRATION THEREOF

CROSS-REFERENCE TO RELATED APPLICATION

This application is the National Stage of, and therefore claims the benefit of, International Application No. PCT/US2010/034086 filed on May 7, 2010, entitled "Handheld Vision Tester and Calibration Thereof," which was published in English under International Publication Number WO 2010/132305 on Nov. 18, 2010, and has a priority date of May 9, 2009 based on provisional application no. 61/176,885 filed by Michael Bartlett, et al. Both of the above applications are commonly assigned with this National Stage application and are incorporated herein by reference in their entirety.

TECHNICAL FIELD OF THE INVENTION

This invention relates to techniques for the design and implementation of a vision testing system including calibration techniques.

BACKGROUND OF THE INVENTION

Vision testing is normally carried out today either through observation of vision testing charts or through professional evaluation including imaging of the inside of the eye and other advanced diagnostic tools. Professional evaluation is effective in analyzing many vision disorders, but is expensive and may not be available in rural and remote areas. Observation of vision testing charts is effective, but is bulky and cumbersome as the charts are normally mounted on a wall and the test subject must observe them from some distance. While limited, use of vision testing charts and professional evaluations are effective for many common vision disorders such as focusing disorders. However, there are some vision diseases, such as diabetic retinopathy, age-related macular degeneration, and other vision diseases where ongoing monitoring of vision is critically important. Such diseases may become active at specific times and, if not treated, could result in irrecoverable vision loss or even blindness.

Consequently, a small and low-cost device that allows patients suffering from these diseases to conveniently monitor their vision is desirable. Techniques that help to ensure such a system operates properly so that it provides dependable test results are highly desirable. And additional techniques such as vision aids that help a patient in their daily life; electronic magnifier functions; auxiliary imaging and display systems; techniques to ensure the patient taking a test is the properly identified and is actively engaged; and other techniques to ensure accurate testing are also desirable.

SUMMARY OF THE INVENTION

To address the above-discussed deficiencies of the prior art, in one embodiment, there is provided a handheld vision tester. In this particular embodiment, the handheld vision tester comprises a display, cursor control, an interface port, and a camera. The display delivers vision tests to a user. The user interacts with the vision tests by using the display and cursor control. The camera verifies that the user takes the vision tests. The interface port allows for communication of the results of the vision tests from the handheld tester to external devices.

In another embodiment, there is provided a method of testing using a handheld vision tester. The method comprises verifying an identity of a user of the handheld device, displaying a series of images on the handheld device, accepting input from the user in response to the series of images displayed on the handheld vision tester, storing the response input in the handheld vision tester, and communicating the response input to a device external to the handheld vision tester.

In yet another embodiment, there is provided a calibration system for use with a handheld vision tester. The calibration system comprises a calibration stand to hold the handheld vision tester and a reflective surface substantially parallel to a display of the handheld device. The calibration stand holds the handheld vision tester at a fixed distance to the reflective surface.

The foregoing has outlined various features of the invention so that those skilled in the pertinent art may better understand the detailed description of the invention that follows. Additional features of the invention will be described hereinafter that form the subject of the claims of the invention. Those skilled in the pertinent art should appreciate that they can readily use the disclosed conception and specific embodiment as a basis for designing or modifying other structures for carrying out the same purposes of the invention. Those skilled in the pertinent art should also realize that such equivalent constructions do not depart from the scope of the invention.

BRIEF DESCRIPTION OF THE DRAWINGS

For a more complete understanding of the invention, reference is now made to the following descriptions taken in conjunction with the accompanying drawings, in which.

DETAILED DESCRIPTION

Figure 1:
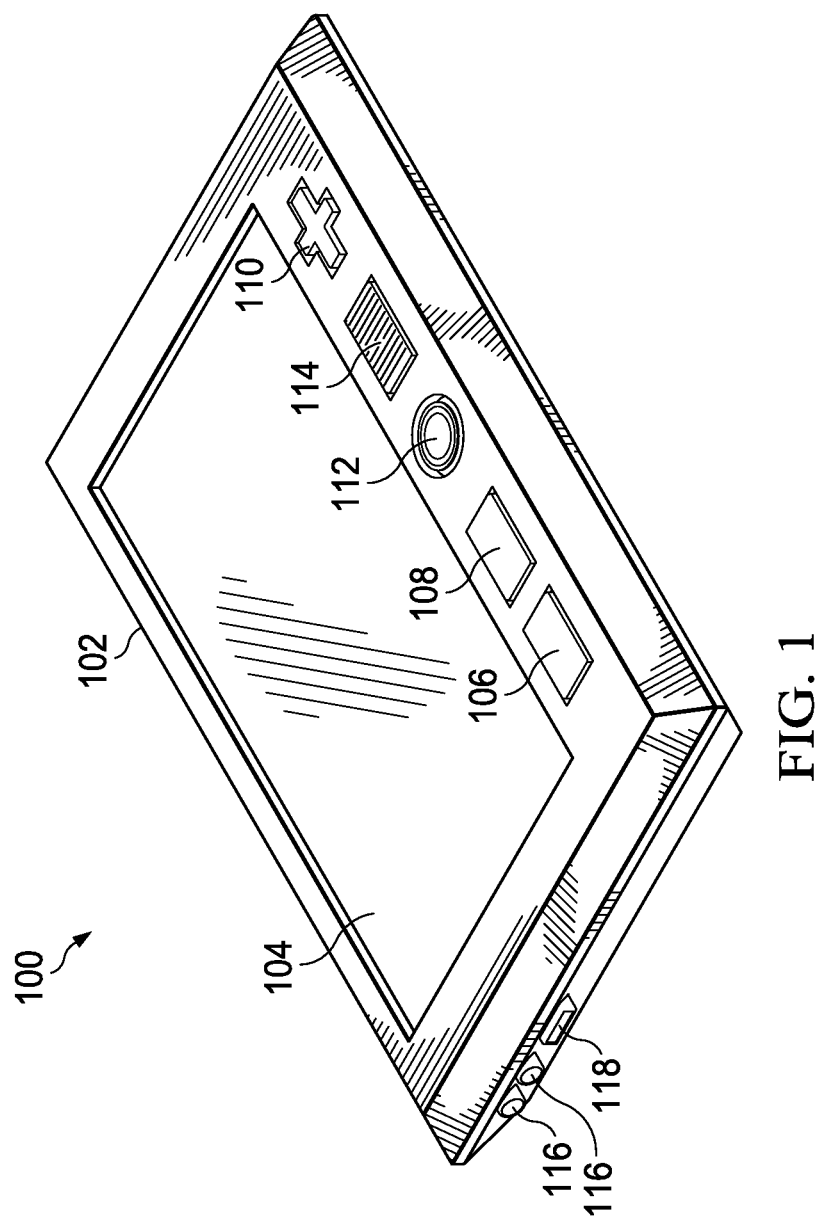
FIG. 1 shows a handheld device suitable for running a vision test.

In FIG. 1, an electronic handheld device 100 is shown. The handheld device 100 may include a case 102, a display 104, a cursor control 110, a fingerprint sensor 114, a camera 112, a first button 106, a second button 108, a power connector 116, and an interface port 118. The display 104 may include touch-screen capability so that the handheld device 100 can be controlled by touching the display 104 in pre-specified locations or manners within certain timeframes. The fingerprint sensor 114 allows the handheld device 100 to identify the person using it. The cursor control 110 is a button that may be pressed to move a cursor across the display 104 and position it in a desired location. Pressing the cursor control 110 may also be used to trigger operations and to control the handheld device 100. Alternative implementations of cursor controls include track balls, joysticks, touch pads, and other approaches may also be used in place of the cursor control 110 as shown in FIG. 1. The first button 106 and the second button 108 may be used to control the handheld device 100 and to operate functions of the handheld device 100. It is noted that the handheld device 100 may be operated through manipulation of the display 104 if a touch-screen capability is included, through the cursor control 110, through the fingerprint sensor 114, through the first button 106 and through the second button 108. Additional buttons and controls are possible including buttons and controls on the sides and back of the handheld device 100. It is also possible to include additional buttons, displays, and other forms of input devices.

The case 102 of the handheld device 100 may be constructed from metals, plastics, or other materials. While not shown in FIG. 1, the handheld device 100 may include removable panels on its front, back, or sides to allow batteries, memory cards, or optional accessories to be installed, connected, or removed. The power connector 116 allows the device to be powered from an external electrical power source that may supply AC or DC power to the handheld device 100. The interface port 118 allows the handheld device 100 to be connected to an external host computer, external cameras, external calibration or test equipment, external accessories, or other systems or devices the user may desire to connect it to. It is also possible that the interface port 118 or the power connector 116 could be configured to supply battery power from the handheld device 100 to an external device or interface connected to them. The interface port 118 may be constructed from multiple physical interfaces and protocols. Some examples are Universal Serial Bus (USB), P1394, Ethernet, RS232, and many other possible interfaces. In addition to the interface port 118, the handheld device 100 may include wireless connectivity. Bluetooth, IEEE802.11, Zigbee, and many other wireless communications protocols and radio electronics may be included in the handheld device 100. The wired and or wireless connectivity of the handheld device 100 allows it to send information to a network service, host computer, or other computing device; and also allows for calibration, configuration, test protocols, software updates, and other useful information to be sent from a host computer or other data processing device or interface to the handheld device 100. The procedure for allowing the handheld device 100 to either send data out over its wired or wireless interfaces or to receive information from other sources should normally include security features to ensure that the users information and privacy are not compromised and also to ensure that configuration, calibration, and other important factors of the handheld device 100 operation cannot be compromised illicitly or accidentally.

The camera 112 can be used to ensure that the same person is taking the test throughout the test sequence and an image of the user can be compared to images from past tests to help ensure that the person taking the test is indeed the correct person. The handheld device 100 can perform this operation by image analysis of an image or images provided from camera 112. Additionally, the camera 112 can be used to check that the user is awake, upright, and appears to be capable and actively engaged in taking the vision test.

In addition to delivering vision tests to a user, the handheld device 100 can also serve as a vision aid to the user. The camera 112 can be used as a still image camera or as a video camera and allow the user to take images and then enlarge them on the display 104 so that they are easier to observe. In addition to enlarging the images, the handheld device 100 can also provide image or video processing capability to sharpen, detail, provide additional contrast, color tint, or otherwise alter the image or video sequence so that it is easier for the user to view it. Of course, additional cameras can be mounted on other parts of the handheld device 100 in addition or in place of the camera 112 shown in FIG. 1. For use as a vision aid, it may be beneficial, for example, to include a second camera on the handheld device 100 that points opposite the direction of the camera 112 shown (that is, this additional camera would point into the page in FIG. 1). Additionally, a camera can be mounted behind the display 104 in place of or in addition to the camera 112 shown in FIG. 1. The camera 112, as shown in the embodiment of FIG. 1, may be beneficial in generating an "enhanced mirror" since it faces the user and can simply put the image it has generated on the display 104 in an enlarged or enhanced view. Special cameras, such as night vision cameras, may also be included in the handheld device 100. Of course, any other wavelength specific camera may be included in the handheld device 100. In addition to displaying information, the handheld device 100 may also include image analysis capability to automatically recognize persons, places, or things by analyzing images taken from the handheld device's 100 camera (or cameras). It is also possible to add auxiliary displays to the handheld device 100 or to use the interface 118 or wireless connectivity to move images and/or video to an external video monitor. Auxiliary displays suitable for use with the handheld device 100 include LCD display panels, CRT displays, light processing display devices, head mounted displays, binocular display devices, virtual reality viewers, and many other types of displays. One example is use of the very small projectors that are now available and can be incorporated into small devices and allow images and video to be expanded for easy viewing. These small projectors are sometimes referred to as pico projectors. Such a pico projector may be physically integrated into the handheld device 100 or may be used as an external separate device connected to the handheld device 100 through a wired or wireless communication link.

The functions of the handheld device 100 shown in FIG. 1 may also be incorporated into electronic handheld devices that are already used for other functions. That is, the function delivered by the handheld device 100 may be implemented on a portable game console, a cellular phone, a personal digital assistant, a netbook computer, a notebook computer, a blood glucose meter, or many other electronic devices. The ability to combine many functions together into a single device allows for convenience for the user and also allows for beneficial combined functionality in some cases. For example, if the handheld device 100 of FIG. 1 includes the function of a glucometer (also known as a blood glucose meter), the user can record their blood glucose level when each vision test is taken so that a more complete record of vision capability and blood glucose can be generated. Of course, other biomedical measurements of a user could also be recorded, such as, but not limited to, blood pressure, heart rate, pupil dilation, iris color changes, eyelash growth, enzyme levels, etc. If the handheld device includes a positioning technology such as the Global Positioning System (GPS), the records of vision testing can be location stamped so that the user can more easily remember where they took each test and what the testing conditions were. Of course, the handheld device 100 can easily include calendar and clock functions so that test results may also be time and date stamped.

Figure 2A:
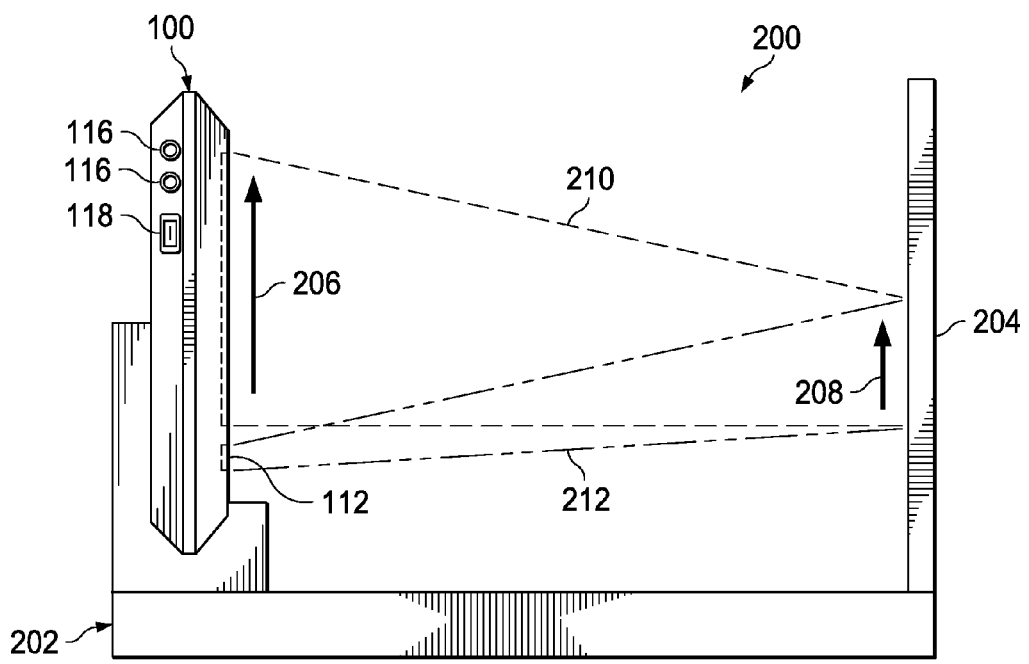
FIG. 2a shows a handheld device mounted in a calibration stand.

In FIG. 2a, a calibration stand 200 is shown with the handheld device 100 mounted in it. The calibration stand 200 comprises a base 202 and a mirror 204. The calibration stand 200 positions the handheld device 100 at a fixed distance and orientation relative to the mirror 204 so that a test image 206 creates a reflection 208 that can be observed by the camera 112 (the camera is not explicitly visible in FIG. 2a, but it's relative position is clear from FIG. 1, so it is identified consistently by the numbering in FIG. 2a). Please note that the test image 206 and the reflection 208 are shown just in front of the handheld device 100 and the mirror 204 in the cross sectional view shown in FIG. 2a. Of course, they would in practice actually appear on the surface of the handheld device's 100 display 104 and, respectively, on the surface of the mirror 204, but such a view is not possible in a cross sectional drawing. The handheld device 100 is inserted into the base 202 and a self-testing and calibration sequence is initiated by the user to ensure that the handheld device 100 is operating properly and can provide good quality measurements. The handheld device 100 can display a wide range of images and observe them back through it's camera to ensure that the shape, color, contrast, size, and other aspects of the images are displayed as they should be. The calibration stand 200 is clearly desirable for such self-testing and self-calibration, but it is noted that this could be undertaken by simply holding the device in front of a reflective surface and initiating the self-testing and calibration sequence. Of course, given the potential for different distances, movement of the handheld device, and other factors, the use of a calibration stand 200 may be preferred.

The base 202 may be fabricated from metals, wood, plastics, or other materials. It may include features such as accurately formed surfaces, keyed openings, mechanical guides, and other features to keep the handheld device 100 accurately and consistently in place. The base 202 may also include fabrics, cushions, gaskets, felt linings, or other features to protect the handheld device 100 from being scratched or damaged when it is inserted and removed from the base 202. And the base 202 may also include mechanical features that secure the handheld device 100 such as straps, clamps, snaps, buckles, or other features. The mirror 204 may be a glass mirror or may be made from polished metals, metal film laminated on plastics or other materials, or may be constructed in other ways to provide a substantially reflective surface. Normally, the mirror 204 would be constructed to be highly reflective of visible light, but in the case that it has limited reflectivity or inconsistent reflectivity for some wavelengths of light, the handheld device 100 may compensate for this limitation through adjustment factors included in its calibration routine. Similarly, if the camera 112 provides higher sensitivity to some wavelengths of light, the handheld device 100 may compensate for it with information about the cameras 112 sensitivity as a function of wavelength.

In another embodiment, the base 202 of calibration stand 200 could include an auxiliary camera in place of mirror 204. In this embodiment, the auxiliary camera would be oriented toward the display of handheld device 100 such that test image 206 is captured by the auxiliary camera. The auxiliary camera could interface with handheld device 100 for calibration purposes or could interface with an external device to analyze calibration of the handheld tester.

The handheld device 100 may keep track of calendar dates and times and require that it be operated through its self-testing and calibration sequence on a regular basis. The user may be reminded electronically of the need for this with visible, audible, or other signals or messages. The handheld device 100 may refuse to operate and collect user test results if it has not been acceptably self-tested and calibrated within a sufficient time interval. Further, if the handheld device 100 detects that it has possibly been modified, the case 102 has been opened, high levels of mechanical shock or acceleration have been measured, or other factors are present that bring the proper condition of the device into question; the handheld device 100 may demand that the user run the self-testing and calibration sequence with acceptable results before further testing takes place.

Figure 2B:
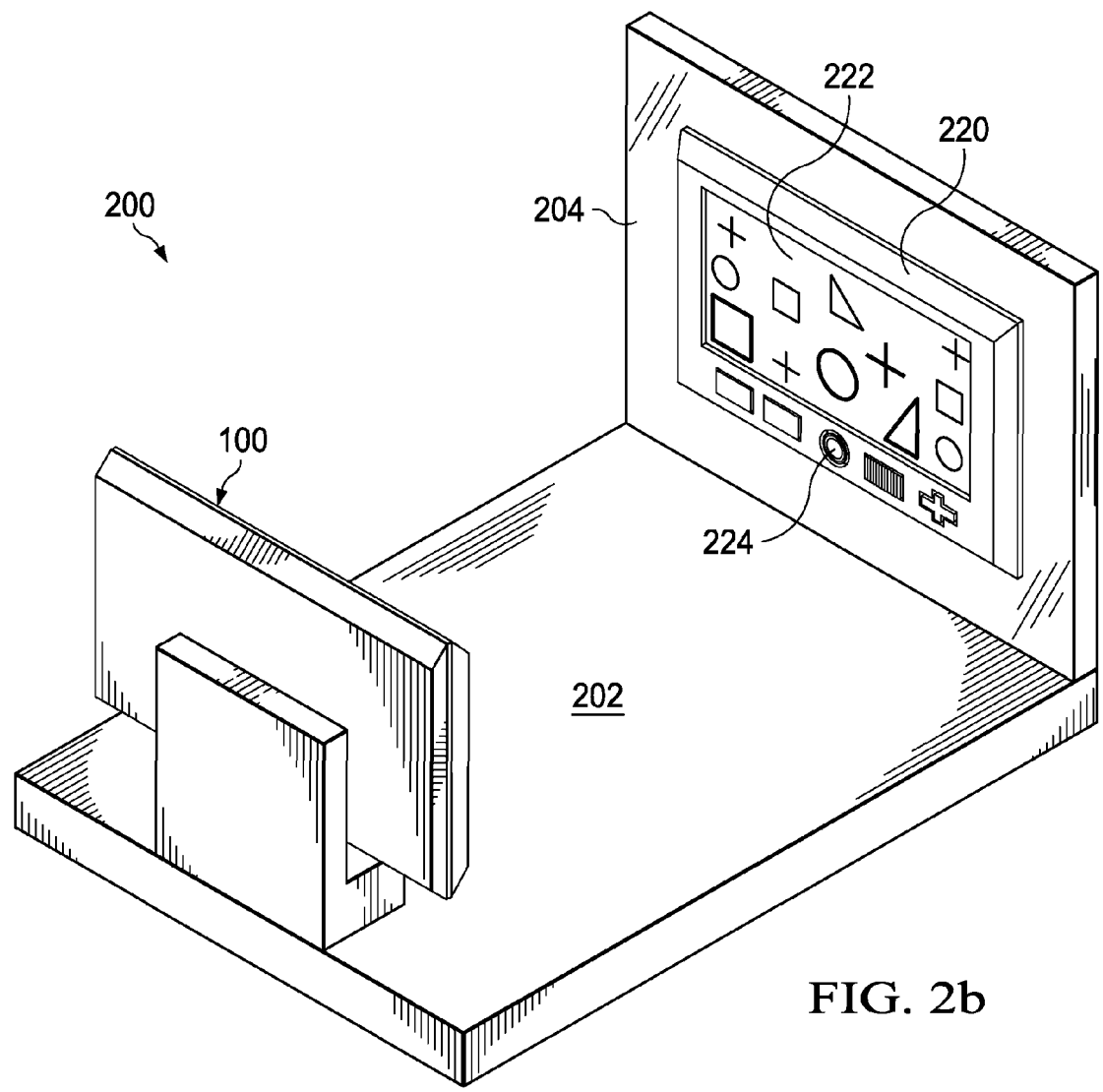
FIG. 2b shows a perspective view of a handheld device mounted in a calibration stand.

FIG. 2b shows a perspective view of a handheld device 100 mounted in a calibration stand 200 including a base 202 and mirror 204. This view is shown to avoid any confusion related to the similar view of a handheld device 100 in a calibration stand 200 shown in FIG. 2a. On the mirror 204, a reflection 220 of the handheld device 100 is visible. This reflection 220 may be analyzed as already described with regard to FIG. 2a by using the camera 112 to create an image of the reflection 220 and use of data processing functions in the handheld device 100 to analyze the calibration image 222 visible in the reflection 220. Note that the camera 112 is not actually visible in FIG. 2b, but the camera reflection 224 of camera 112 is visible. The generation of a calibration image 222 will be discussed next with regard to FIG. 2c.

Figure 2C:
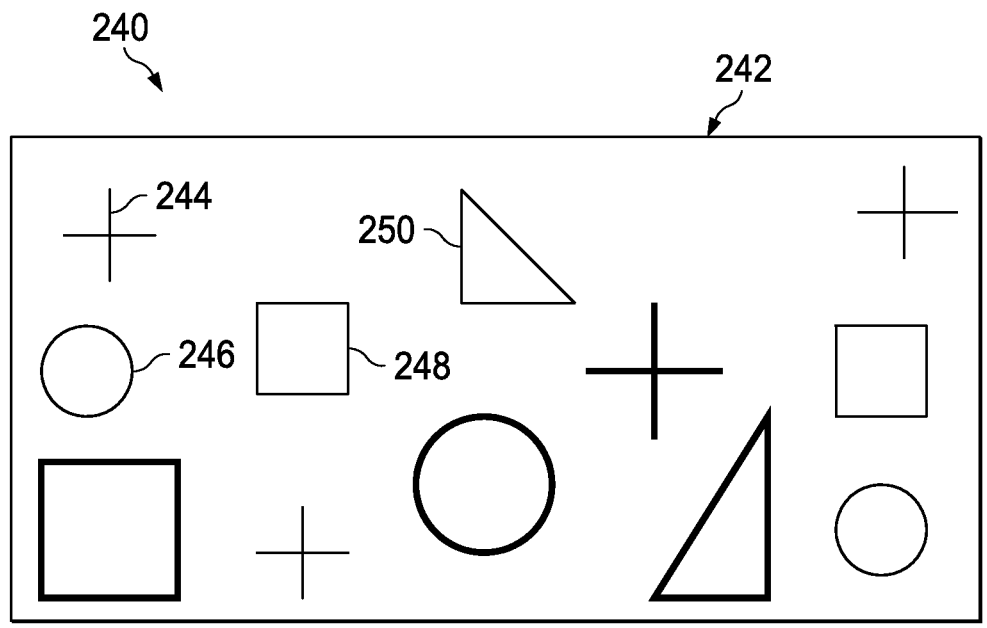
FIG. 2c shows an image suitable for use for calibration.

FIG. 2c shows a calibration image 240 that may be used for calibration and testing of the handheld device 100 either through use of the calibration stand 200 or with a reflective surface as described above. In the course of testing and calibrating the handheld device 100, a calibration image 240 is displayed on the display 104 and the reflection of the calibration image 240 is observed with a camera 112. A very wide variety of calibration images 240 may be used. The calibration image 240 shown in FIG. 2c includes crosses 244, circles 246, squares 248, and triangles 250 inside display boundary 242. The shapes shown in the calibration image 240 are shown in black and white for convenience. However, a very wide variety of shapes, images, features, shadings, textures, colors, line weights, and other aspects may be used in an image for calibration and handheld device 100 testing purposes. For example, rectangles, wavy lines, ellipses, trapezoids, and very many other shapes and images displayed in all possible colors, shadings, brightness levels, and other factors may be used as test images or as part of a test image. And, in addition to stationary images, moving images and video images may be used. Many standard video and image calibration charts may also be used.

Figure 3:
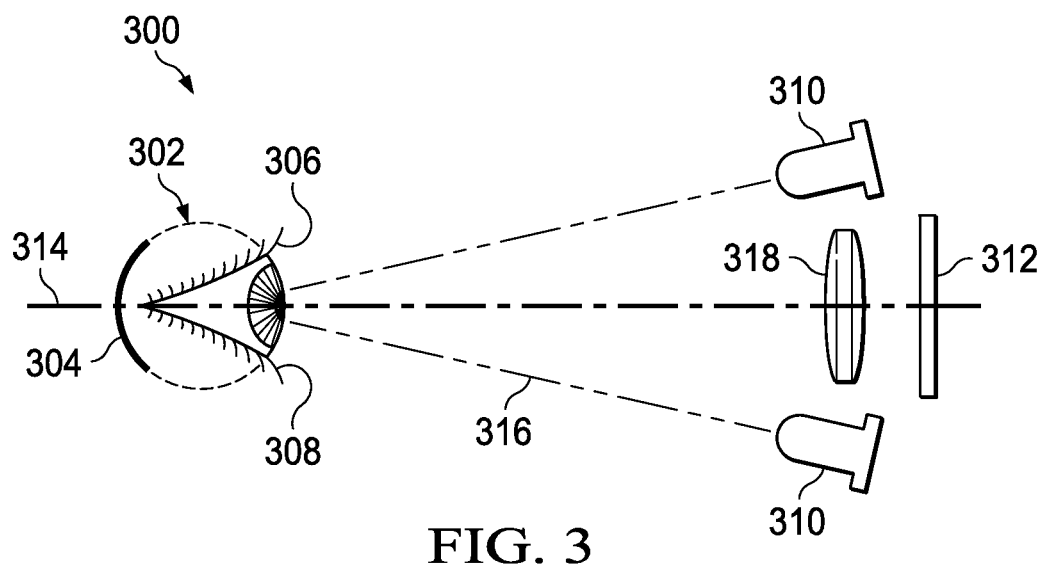
FIG. 3 shows a fundus imaging system

FIG. 3 shows a fundus imaging system 300. A cross section of an eyeball 302 and a schematic of how illumination might be applied so that fundus photos of the retina 304 may be taken are shown. Fundus photography is widely used to take images of the retina 304 of the eyeball 302. Fundus photos are taken by using special lighting systems to illuminate the inside of the eye and to then take a photograph of the retina 304 through the pupil of the eyeball 302. In FIG. 3, light emitting diodes 310 are shown to illuminate the inside of the eye. Other lighting techniques are possible such as scanning lasers, incandescent bulbs, and other techniques. Light emitting diodes 310 are presently preferred for their small size, low cost, and high efficiency. While only two light emitting diodes 310 are shown in FIG. 3, the actual embodiment might include a full circle of light emitting diodes 310 around the lens 318 and imager 312. Many possible forms of the camera 112 of the handheld device 100 are possible, but most are based on a simple lens 318 and imager 312. Many types of imagers such as CMOS image sensors, CCD (Charge Coupled Device) imagers, and other imagers may be used. Also, the lens 318 may be a fixed lens or a variable focal length lens and may be formed from glass, plastic, or other possible materials. It is noted that the camera function made up of the lens 318 and imager 312 may be those of the camera 112 shown in FIG. 1 or may be a separate camera mounted in the handheld device 100 or may be a separate camera that is connected electronically or can pass its image to the handheld device 100. FIG. 3 also includes a schematic feature of the upper eyelash 306, the lower eyelash 308, a diagram center line 314, and illumination reference lines 316.

The addition of a fundus imaging system 300 to the handheld device 100 opens the possibility to couple analysis of an image of the retina 304 with the results of vision testing. If areas of the vision field are determined to show distortion, reduced clarity, limited acuity, or other effects, these can be compared to areas of the retina corresponding to that area of the vision field. In this way, automated or professional analysis of the fundus image can include additional attention in areas where the vision field showed limited or poor performance. And, in a reverse fashion, areas of the fundus image that show signs of eye disease can be given additional attention in the automated vision testing. The combination of both vision testing and fundus image analysis is novel and is a key aspect of some possible embodiments of this invention.

Although the description above contains many specificities, these should not be construed as limiting the scope of the invention, but as merely providing illustrations of some of the presently preferred embodiments of this invention. Thus the scope of the present invention should be determined by the appended claims and their legal equivalents, rather than by the examples given. Those skilled in the art to which this application relates will appreciate that other and further additions, deletions, substitutions and modifications may be made to the described embodiments.

What is claimed is:

1. A handheld vision tester, comprising:
a display,
a cursor control;
an interface port; and
a camera;
wherein;
said display delivers vision tests to a user;
said user interacts with said vision tests by using said display and cursor control;
said camera verifies said user takes at least one of said vision tests and verifies an identity of said user; and
said interface port allows for communication with external devices of results of said vision tests.

2. The handheld vision test as recited in claim 1, wherein said display includes a touchscreen display.

3. The handheld vision tester as recited in claim 1, further comprising a fingerprint sensor to assist in identifying said user.

4. The handheld vision tester as recited in claim 1, further comprising buttons for said interaction.

5. The handheld vision tester as recited in claim 1, wherein said communication with external devices allows for a record of vision testing results including time and date of each of said vision tests to be stored.

6. The handheld vision tester as recited in claim 1, further comprising a wavelength specific camera.

7. The handheld vision tester as recited in claim 1, further comprising a measurement means for a biomedical measurement of said user.

8. The handheld vision tester as recited in claim 7, wherein a result of said biomedical measurement of said user is combined with said results of vision tests.

9. The handheld vision tester as recited in claim 7, wherein said biomedical measurement of said user is a blood glucose level.

10. The handheld vision tester as recited in claim 9, wherein a result of said biomedical measurement of said user is combined with said results of vision tests.

11. A method of testing vision using a handheld vision tester, comprising:
verifying an identity of a user of said handheld vision tester;
displaying on said handheld vision tester a series of images to said user;
accepting input in response to said series of images from said user;
storing said response input in said handheld vision tester; and
communicating said response input to a device external to said handheld vision tester.

12. The method as recited in claim 11, wherein said verifying said identity uses a fingerprint sensor or a camera of said handheld vision tester.

13. The method as recited in claim 11, further comprising verifying said user is awake, upright, and appears to be capable and actively engaged in said vision testing.

14. The method as recited in claim 11, further comprising communicating a time and date of said accepted input along with said response input to said device external to said handheld vision tester.

\* \* \* \* \*